(12) United States Patent
Ballinger, Jr.

(10) Patent No.: US 6,743,440 B1
(45) Date of Patent: Jun. 1, 2004

(54) POLYCYCLIC QUINONE AND IONOPHORE COMPOSITION FOR THE SYNERGISTIC REDUCTION OF METHANE FORMATION IN RUMINANT ANIMALS

(75) Inventor: Kenneth E. Ballinger, Jr., Kennett Square, PA (US)

(73) Assignee: Arkion Life Sciences LLC, Wilmington, DE (US)

( * ) Notice: Subject to any disclaimer, the term of this patent is extended or adjusted under 35 U.S.C. 154(b) by 302 days.

(21) Appl. No.: 09/685,269

(22) Filed: Oct. 10, 2000

Related U.S. Application Data
(60) Provisional application No. 60/159,478, filed on Oct. 14, 1999.

(51) Int. Cl.⁷ .......................... A23K 1/165; A23K 1/17
(52) U.S. Cl. ...................... 424/442; 514/192; 514/199
(58) Field of Search .................... 424/442; 514/192, 514/199

(56) References Cited

U.S. PATENT DOCUMENTS

| | | | |
|---|---|---|---|
| 4,237,116 A | * 12/1980 | Gillin et al. | 424/117 |
| 5,175,319 A | 12/1992 | Hudson et al. | 552/297 |
| 5,385,844 A | 1/1995 | Kennamer et al. | 436/13 |
| 5,648,258 A | 7/1997 | Odom | 435/252.1 |

FOREIGN PATENT DOCUMENTS

| | | |
|---|---|---|
| WO | WO 94/08738 | 4/1994 |
| WO | WO 96/14062 | 5/1996 |

OTHER PUBLICATIONS

In Vitro Inhibition of Microbial Methane Production By 9,10–Anthraquinone, Garcia–Lopez, et al., Delaware Agricultural Experiment Station, Department of Animal and Food Sciences, University of Delaware, Newark 19717–1303 and Central Research and Development, E.I. Dupont De Nemours & Co., Wilmington, DE 19880, pp. 2276–2284.

* cited by examiner

*Primary Examiner*—Dwayne Jones
*Assistant Examiner*—C. Delacroix-Muirheid
(74) *Attorney, Agent, or Firm*—Basil S. Krikelis

(57) ABSTRACT

A composition, preferably used to reduce methane formation in a ruminant, wherein the composition is a combination of a polycyclic quinone compound and an ionophore compound.

15 Claims, No Drawings

POLYCYCLIC QUINONE AND IONOPHORE COMPOSITION FOR THE SYNERGISTIC REDUCTION OF METHANE FORMATION IN RUMINANT ANIMALS

RELATED APPLICATIONS

This application claims the benefit of U.S. Provisional Application No. 60/159,478 on Oct. 14, 1999.

BACKGROUND OF THE INVENTION

Control of methane production by methanogenic bacteria in ruminant animals has important agronomic impact. Use of inhibitors to control the methane produced by ruminants has been recognized as a part of the mechanism for feed efficiency that results when mixed with cattle feed for both dairy and meat production. An effective additive to boost ruminant feed efficiency is a well-established part of the agronomic practice for commercial ruminant farming.

Methanogenic bacteria form methane by an anaerobic process. The group comprises the genera Methanococcus, Methanobacterium, Methanosarcina, Methanobrevibacter, Methanothermus, Methanothrix, Methanospirillum, Methanomicrobium, Methanococcoides, Methanogenium and Methanoplanus.

Inhibitors of methanogenesis in rumen perform two important functions. Cows and sheep lose 5–10% of their caloric intake to the formation of methane and the resulting loss of a carbon molecule that could have been incorporated in short chain fatty acid production. Inhibition of methane will, therefore, have a direct effect on the formation of short chain fatty acids in the rumen. Other investigators have reported the positive effect of inhibiting methane in rumen fermentation (C. J. Van Nevel, D. I. Demeyer, Manipulation of rumen fermentation, In: The Rumen Microbial Ecosystem, P. N. Hobson, and (Ed) Elsevier Publishing Co. (1988)).

Methane inhibitors have previously been developed for feedstock additives to increase feed efficiency. The inhibitors fall generally into two classes. The first class induces those that affect methane formation indirectly by interfering with the electron flow upstream of the methanogen in the microbial food chain. Examples of this group would be nitrates and nitrites. The second class includes those that affect methanogens directly. Examples of such compounds are ionophores, antibiotics, and polycyclic quinones. Ionophores include, for example, RUMENSIN® (monensin sodium), lasalocid A, salinomycin, avoparcin, aridcin, actaplanin, and penicillin. A more complete list is cited in: C. J. Van Nevel, D. I. Demeyer, Manipulation of rumen fermentation, In: The Rumen Microbial Ecosystem, P. N. Hobson, and (Ed) Elsevier Publishing Co. (1988). Polycyclic quione activity in this regard are referenced in U.S. Pat. No. 5,648,258 (Odom).

The inhibition of methane in rumen by polycyclic quinones (PCQ) operates by a different mechanism than ionophores. PCQ's are redox catalysts that block reduction of electron receptors at the cytochrome c-3 site in the cell wall of anaerobic bacteria, such as methanogens and sulfate reducers. Weimer reveals the action of 9,10-anthraquinone in U.S. Pat. No. 5,385,844 as it applies to reducing sulfate by sulfate reducing bacteria.

Ionophores act as antibiotics with the result that target bacteria concentrations in the rumen are reduced. Since 9,10-anthraquinone does not reduce target bacteria concentration in the rumen, the two mechanisms are clearly distinct.

Garcia-Lopez et al. has demonstrated the use of PCQ's and ionophores each separately can reduce biogenic methane. (P. M. Garcia-Lopez, L. Kung, Jr., J. M. Odom "In Vitro Inhibition of Microbial Methane Production by 9,10-anthraquinone". Journal of Animal Science 1996, 74:2276–2284).

SUMMARY OF THE INVENTION

In its primary aspect, the invention is directed to a synergistic method for reducing methane formation in the rumen of ruminants comprising administering to the ruminant at least one ionophore compound, and at least one polycyclic quinone compound.

DEFINITIONS

As used herein, the term "rumen" refers to the gastrointestinal section found in ruminants (i.e. cattle, deer, moose, camels, sheep, goats, oxen, water buffalo, and musk oxen) where food is partially digested through bacterial fermentation.

DETAILED DESCRIPTION OF THE INVENTION

A. In General

It is recognized that the administration of an ionophore compound or the administration of a polycyclic quinine (PCQ) to a ruminant will reduce methane and boost feed efficiency in the ruminant. However, applicant has discovered that when the two classes of compounds (ionophores and PCQ's) are administered simultaneously to a ruminant, a synergistic reduction of methane occurs. The advantage of employing this technique is to provide additional feed efficiency for agronomic benefits in ruminant raising. In addition, the levels of antibiotics in feed can be reduced which helps lower the adaptive challenge by non-target bacteria in the rumen and, thereby, lessens the likelihood of adaptation and resistance by rumen bacteria to the antibiotic.

B. Polycyclic Quinones (PCQ's)

A wide variety of polycyclic quinones can be used in the invention. As used herein, the term "polycyclic quinone" or "PCQ" refers to bicyclic, tricyclic and tetracyclic condensed ring quinones and hydroquinones, as well as precursors thereof. On the whole, the non-ionic polycyclic quinones and polycyclic hydroquinones (herein referred to collectively as PCQ's) have very low solubility in water at ambient temperatures. For use in the invention, it is preferred that such PCQs have water solubility no higher than about 1000 ppm by weight.

In addition, as noted above, certain precursors of such PCQ's can also be used in the invention either combined with the relatively insoluble PCQ's or by themselves. Such precursors are anionic salts of PCQ's, which are water soluble under alkaline anaerobic conditions. However, these materials are not stable and are easily converted to the insoluble quinone form upon exposure to oxygen.

Among the water-insoluble PCQ's, which can be used in the invention, are anthraquinone compounds. As used herein, the term "anthraquinone" or "AQ" refers to 9,10-anthraquinone, naphthoquinone, anthrone (9,10-dihydro-9-oxo-anthracene), 10-methylene-anthrone, phenanthrene-quinone and the alkyl, alkoxy and amino Derivatives of such quinones, 6,11-dioxo-1H-anthra[1,2-c]pyrazine, 1,2-benzanthraquinone, 2,7-dimethylanthraquinone, 2-methylanthraquinone, 3-methylanthraquinone, 2-aminoanthraquinone and 1-methoxyanthraquinone. Of the foregoing cyclic ketones, 9,10-anthraquinone and methylanthraquinone are preferred because they appear to be more effective. Naturally occurring anthraquinones can be used as well as synthetic anthraquinones.

"Anthraquinone" or "AQ" compounds can further include insoluble anthraquinone compounds, such as 1,8-dihydroxy-anthraquinone, 1-amino-anthraquinone, 1-chloro-anthraquinone, 2-chloro-3-carboxyl-anthraquinone, 1-hydroxy-anthraquinone and unsubstituted anthraquinone. Various ionic derivatives of these materials can be prepared by catalytic reduction in aqueous alkali.

In addition, a wide variety of anthrahydroquinone compounds can be used in the method of the invention. As used herein, the term "anthrahydroquinone compound" refers to compounds comprising the basic tricyclic structure, such as 9,10-dihydroanthrahydroquinone, 1,4-dihydroanthra-hydroquinone, and 1,4,4a,9a-tetrahydroanthrahydro-quinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water-soluble forms are stable only in high pH anaerobic fluids. Low pH fluids (pH less than about 9–10) will result in the formation of the insoluble molecular anthrahydro-quinone. Aerobic solutions will incur oxidation of the anthrahydroquinones to anthraquinone. Thus, anthrahydro-quinones will not exist for long periods of time in an aerated environment. For these reasons, anthrahydroquinone treatments are usually implemented with the soluble ionic form in a caustic solution. Sodium hydroxide solutions are preferred over the hydroxides of other alkali metals for economic reasons. Rumen physiology may limit the pH of such a preparation, but use of sodium hydroxide in ruminant feed is an established practice.

The extraordinary effectiveness of various forms of anthraquinone lies in their non-reactivity. These products are transported into the biofilm, diffuse through the biofilm voids, and then diffuse or are randomly transported by Brownian motion into the bacterial microcolonies without reduction in concentration as a consequence of a exopolysaccharide matrix present in the biofilm.

Even though solid particles of polycyclic quinone (PCQ) are required to inhibit the methane-producing bacteria, the PCQ can be introduced into the microbial environment in several physical forms. The PCQ can be introduced as a dispersion of these solid particles throughout the feed at the appropriate dose. The ionic (sodium salt) form of the PCQ will allow it to be solubilized in an anaerobic caustic solution as long as the pH is greater than 12 and preferably greater than 13. The salt stays soluble if the pH of the solution remains above about 12, with precipitation of solid PCQ taking place as the pH is reduced below this value. In the soluble form or with a slight amount of precipitated PCQ (typically in colloidal form), anthraquinone is in molecular form or consists as extremely small (submicron-sizes) particles. When the PCQ added to the water is in the form of a suspension of finely divided particles, it is preferred that their largest dimension be no greater than 50 micrometers, and preferably no greater than 5–10 micrometers so that they can more easily pass through biofilm.

Whether the soluble or insoluble anthraquinone is used, it has been observed that the functional attachment of the anthraquinone particles to the bacteria is limited in time by metabolism of the particles by the sulfate-reducing bacteria. Thus, application of the treating medium must be repeated periodically in order to maintain inhibition effectiveness.

Unlike antibiotics, which are lethal to rumen based bacteria, especially methanogens, PCQ's are non-lethal in their mechanism. Studies by Cooling et al. have revealed the mechanism of action of anthraquinones in sulfate-reducing bacteria (F. B. Cooling III, C. L. Maloney, En. Nagel, J. Tabinowski and J. M. Odom. "Inhibition of Sulfate Respiration by 1,8-Dyhydroxy-Anthraquinone and other Anthraquinone Derivatives". Applied And Environmental Microbiology, August 1996, p. 2999–3004). PCQ's block the production of adenosine triphosphate by the bacteria and thereby inhibit respiration using sulfate as an electron acceptor. The sulfate-reducing bacteria respire by alternate mechanisms under these conditions and are not killed. SRBs and methanogens are closely linked in their ecological niche in the rumen and other anaerobic environments. The PCQ effect on methanogens is either a direct effect similar to the SRB mode of action or indirect since methanogens are dependent on SRB for micro-nutrients. In both conditions, methanogens thrive in the presence of PCQs without forming the normal levels of methane.

C. Ionophores

Compounds known as ionophores are generally defined as substanced that facilitate transmission of an ion, (such as sodium), across a lipid barrier such as a cell membrane. Two ionophore compounds particularly suited to this invention are the RUMENSIN® (monensin sodium) product from Eli Lilly which is a sodium salt of a complex molecule of the general formula C36H61011NA (formula weight 692.9) and lasalocid A from Hoffman LaRoche. Other ionophore compounds are discussed in the Background Section of this application, and include salinomycin, avoparcin, aridcin, actaplanin and penicillin among others. In the rumen, ionophores act as effective antibacterial agents. Killing methane producing bacteria in the rumen of cattle decreases the loss of carbon from the rumen fluid as methane which is a similar action to AQ.

Inhibition of methane by ionophores follows a mode of action where methanogens and other bacteria that produce pure hydrogen and carbon dioxide are reduced in concentration. The antibacterial action of ionophores is the direct cause of the reduction in methanogenesis (P. M. Garcia-Lopez et al., 1996 In Vitro Inhibition of Microbial Methane Production by 9,10 anthraquinone: Delaware Agricultural Experimental Station, paper no. 1567). Reduction in bacteria concentration in the rumen can also affect other microlife that is generally helpful in rumen digestion and the formation of short chain fatty acids. The short chain fatty acids are the source of energy required by ruminants. Increases in concentrations of proprionate and sometimes butyrate are accompanied by reductions in acetate in rumen affected by ionophores. Ionophores tend to lower concentrations of bacteria that produce hydrogen, which is contrary to the results seen with PCQ's. Hydrogen values tend to increase with PCQ's, which should lead to stimulation of bacteria levels that process hydrogen into butyrate. (*B.fibrisolvens*). Acetate forming bacteria are also reduced with ionophores where PCQ's would tend to stimulate the formation of more acetate if acetogenic bacteria such as (*Acetitomaculum ruminis*)[2] (Greening and Leedle, 1989 Enrichment and Isolation of *Acetitonaculum Ruminis* gen.nov.sp. Nov; Acetogenic Bacteria from the Bovine Rumen. Arch. Microbial. 151:399) are present. The advantage of increased bacterial formation of short chain fatty acids is a boost in the food value of the feed ruminants.

D. Methods of Operation

The function of the PCQ is to act as an inhibitor specific for methanogens and sulfate reducers found naturally in rumen fluid. Anthraquinone (AQ) is the preferred PCQ to be used in the invention. The inhibition of methane by AQ is a separate and distinct mechanism from the antibiotic effect of an ionopbore compound, such as monensin sodium. Bacteria counts of methanogens are not affected by 9,10-anthraquinone while ionophores reduce the viability of methanogens. Therefore, the actions of the two classes of compounds are distinct and an additive effect would be expected. Contrary to expectations, the results show synergistic effects.

The customary method of adding a feed additive is to premix the compound with a binder and a carrier so that the premix carries a diluted concentration of active ingredient. The premix is blended with the rations for the animal in a subsequent process so that there is a certified final concentration of active ingredient in the feed. A further method of adding PCQ to animal rations would be a direct admixture of active ingredient with the rations by means of a liquid formulation sprayed onto the feed or by a dry formulation admixed by blending. The use of a sodium salt of anthraquinone in a high pH medium could also be used as a way to enhance the distribution of AQ in animal feed. Certain feeds would have nutritive improvement due to the delignification of the fibers caused by the well known action of a high pH medium and the catalytic action of AQ on the lignin bonds that make fiber less digestible.

The preferred concentration of ionophores such as monensin sodium, 2,2-dichloracetamide is preferably in the range of 0.5 ppm–35 ppm and more preferably in the range of 5–10 ppm in the rumen fluid of the ruminant. AQ is preferably in the range of 10–500 ppm and more preferably in the range of 10–100 ppm in the rumen fluid of the ruminant.

The advantageous properties of this invention can be further observed by reference to the following examples, which illustrate the invention.

EXAMPLES

Example 1

Culture Conditions

Effects of the potential methane inhibiting compounds were studied in in vitro batch culture ruminal fermentations. In all experiments, the treatment designated as "control", was a complete early market lamb feed (Agway, Inc., Tully, N.Y.) that was ground to pass through a 1-mm screen of a Wiley Mill (Arthur H. Thomas, Co., Philadelphia, Pa.) and contained 0.29% sulfur (dry matter basis). In treatments with "high sulfur" levels, the control was supplemented with $Na_2SO_4$ to yield a final concentration of 1.09% (dry matter basis). Sufficient control and high sulfur feed was prepared at the start of the study and was used in all experiments. A representative sample of each diet was analyzed for nutrient content by a commercial laboratory (Cumberland Valley Analytical Services, Maugansville, Md.). The composition of the diets is shown in Table 1. Batch culture fermentations were replicated in triplicate 60 ml serum bottles for each treatment and (or) sampling point and contained 0.375±0.005 g of appropriate diet (air dry basis).

Rumen fluid was obtained from a 300 kg fistulated steer with a rumen fistula. The steer had limited access to a commercial calf starter (18% CP) via a computer feeder and had ad libitum access to a medium quality alfalfa hay. Care and handling of the steer followed the standards outlines in the Agricultural Animal Care and Use Handbook (Consortium, 1989). Ruminal fluid was collected approximately 4 h after the morning allocation of hay and contents were placed in a sealed thermos while being transported to the lab for processing. Within 15 min of collection, ruminal fluid was filtered through four layers of cheese cloth and placed into a re-pipette dispenser that had been purged with anaerobic grade $CO_2$ (<1 ppm $O_2$). An equal volume of warm (39° C.) mineral-buffer solution (Goering and Van Soest, 1970) was added to the rumen fluid. A reducing solution was added where noted. In all experiments, 29.5 ml of the rumen fluid—buffer solution and 0.5 ml of appropriate treatment solution (when called for) was added to each serum bottle for each treatment. The serum bottles were then purged with anaerobic grade $CO_2$ for 10 sec and sealed with a butyl-rubber stopper and seal crimp. Serum bottles were incubated in a shaking water bath (New Brunswick Scientific, model G76, set at speed 2.5) for 24 h at 40° C.

Treatment

In order to establish an optimum sampling time in subsequent experiments, the high sulfur diet was placed in nine serum bottles, incubated as described, and three bottles sampled at 6, 12, and 24 hours (Experiment 1).

Treatments were: 1) C; 2) HS; 3) HS plus 10 ppm AQ; 4) HS plus 5 ppm RUMENSIN® (Elanco, Greenfield, Ind.) and 5) HS plus 10 ppm AQ. Fermentations supplemented with RUMENSIN® were prepared by first dissolving the RUMENSIN® in 96% ethanol and then adding the same volume of deionized water, yielding a concentration of monensin (in 48% ethanol) that would result in 5 ppm in the rumen fluid-buffer mix when 0.25 ml of the solution was added to 29.5 ml of the rumen fluid-buffer solution; finally, 0.25 ml of deionized water was added to yield a final volume of 30 ml. Each of the other treatment conditions (including the control fermentations) were modified by adding the same amount of ethanol to each as was present in the RUMENSIN® fermentation. This was done by doubling the concentration of the stock solutions, adding 0.25 ml of the stock solution (or deionized water for the controls) and 0.25 ml of 46% ethanol.

Analyses

Incubation was stopped after 24 hr by immersing the serum bottles in ice. The total volume of gas produced was measured by noting the volume of water displaced in an inverted burette and adding the amount of volume. Gas volume measurements were completed within 20 min of each other. To this value, was added the volume of the head space of the serum bottle. Three milliliters of the gas were then transferred to a vacutainer tube for methane and hydrogen analysis. The presence of methane and hydrogen were determined by gas chromatography. Two hundred microliters of the gas sample was injected onto a Hewlett Packard (Avondale, Pa.) 5880A gas chromatograph fitted with a Porapak Q column using argon as the carrier gas with a flow rate of 11.1 ml/min, and a thermal conductivity detector. Initial oven settings were at 90° C. for 1 minute followed by a rate increase of 30° C./min until a final temperature of 190° C. was reached. This temperature was maintained for 6 min. Analyses of gas and liquid sulfide were completed within two hours of the sample collection.

The pH of the final fermentation fluid was determined by pH probe. The fermentation fluid was then acidified with 1.0 ml of 25% meta-phosphoric acid (containing 10 ppm iso-caproic acid as an internal standard) to 5.0 ml of the fermentation fluid. The acidified fermentation fluid was analyzed for ammonia via a phenol-hypochlorite method as described by Okuda et al. (1965). The VFA were determined on a Hewlett Packard 5890A gas chromatograph using a 530 $\mu$m macro bore Carbowax M column (Supelco, Bellfonte, Pa.). The chromatograph oven was programmed as follows 70° C., for 1 min, 5° C. increase/min to 100° C., 45° C. increase/min to 170° C., and final holding time of 5 min. Total VFA (TVFA) concentration was calculated as the sum of all VFA. The molar proportions of VFA was calculated by dividing the individual VFA by the sum of the TVFA.

Statistical Analysis

The experiments were replicated on two separate days. Data were analyzed using the general linear model procedure of SAS (1985). The main effect of treatments were tested using the type III mean squares as the error term. When a significant F test was detected, means were compared by Turkey's test. Significance was declared at P<0.05 unless otherwise noted.

Dose Effect of 9,10-Anthraquinone on In Vitro Ruminal Fermentation

Experiment 1

The effects of 9,10 AQ on in vitro fermentation are shown in Table 1: Total VFA was numerically but not statistically decreased by AQ relative to the control and untreated high sulfur diet. In general, the low level of 9,10 AQ (1 ppm) had no effect on fermentation end-products when compared to the untreated diets. However, both the intermediate and high levels of 9,10 AQ decreased (P<0.05) the molar proportion of C2 and total gas produced but increased the percentages of C3, C4 and C5. These amounts of 9,10 AQ also increased (P<0.05) pH and the highest level decreased (P<0.05) ammonia-N. When compared to the control diet, addition of 10 and 25 ppm 9,10 AQ decreased methane production by 21 and 41%, respectively, but hydrogen concentration was unaffected by treatment.

Effect of Various Compounds on In Vitro Fermentation

The effect of ionophore alone and in combination with 9,10 AQ compared to 9,10 AQ alone and $MoO_4$ alone in diets with high sulfur are shown in Table 1. The methane production shows the most dramatic synergy. Methane inhibition is the best measurement of how compounds will improve the digestive benefit of methane inhibitors such as AQ and ionophores.

Results

|  | Methane Concentration Umole/24 hr. fermentation | Percent of Control |
|---|---|---|
| Control | 403 | — |
| AQ 10 ppm | 265 | 66% |
| Ionophores 5 ppm | 299 | 74% |
| AQ plus Ionophore 10 + 5 ppm | 155 | 38% |

AQ plus Ionophore is synergistic by the following calculation:

Methane Concentration

AQ alone: 66% of control
Ionophore alone: 74% of control
Expected result if
Additive in effect: >50% of control (66% times 74%=49%)
Actual result of
Combined effect: 38%
38% is statistically significant and lower than expected

What is claimed is:

1. A composition comprising at least one polycyclic quinone and at least one ionophore compound, wherein said polycyclic quinone and said ionophore compound act synergistically to reduce methane formation.

2. The composition of claim 1 wherein the polycyclic quinone further comprises an anthraquinone or anthrahydroquinone compound.

3. The composition of claim 1 wherein the ionophore compound is selected from the group consisting monensin sodium, lasalocid A, salinomycin, avoparcin, aridcin actaplanin and penicillin.

4. The composition of claim 1 wherein the ionophore compound is monensin sodium.

5. A method for synergistically reducing methane formation in the rumen of a ruminant, the method comprising

TABLE 1

Effect of Compounds on in vitro fermentation (Experiment 1)

| Treatment | TVFA[1] | VFA[2] | | | | | | pH | $NH_3$—N mg/dl | Total Gas[3] | Methane | Hydrogen |
| | | C2 | C3 | Ci4 | C4 | Ci5 | C5 | | | | | |
|---|---|---|---|---|---|---|---|---|---|---|---|---|
| Control[6] | 127.8[a] | 55.3[b] | 24.1[c] | 1.1[b] | 15.2[c] | 1.6[b] | 2.7[d] | 6.02[c] | 38.1[a] | 94.1[ab] | 403[a] | 3.77[b] |
| High Sulfur (S)[7] | 129.5[a] | 56.1[a] | 23.7[d] | 1.0[b] | 15.0[c] | 1.6[b] | 2.6[d] | 6.00[c] | 36.8[a] | 97.1[a] | 465[a] | 4.15[ab] |
| High S + AQ[8] 10 ppm | 118.0[c] | 48.4[d] | 28.1[b] | 1.2[ab] | 17.3[a] | 1.7[b] | 3.3[b] | 6.15[bc] | 37.2[a] | 89.2[cb] | 265[b] | 4.27[ab] |
| High S + $MoO_4$ 25 ppm | 123.9[b] | 55.2[b] | 24.2[c] | 1.2[b] | 15.1[c] | 1.6[b] | 2.7[d] | 6.00[c] | 37.9[a] | 94.1[ab] | 451[a] | 4.13[ab] |
| High S + M[9] 5 ppm | 117.5[c] | 52.4[c] | 28.0[b] | 1.3[ab] | 13.6[d] | 1.7[b] | 3.0[c] | 6.30[ab] | 36.0[a] | 85.2[c] | 299[b] | 4.17[ab] |
| High S + M + AQ 5 + 10 ppm | 107.3[d] | 44.2[e] | 33.1[a] | 1.4[a] | 15.4[b] | 2.0[a] | 4.0[a] | 6.36[a] | 38.7[a] | 74.2[d] | 155[c] | 7.35[a] |
| SE[10] | 0.8 | 0.1 | 0.1 | <0.1 | 0.1 | <0.1 | <0.1 | 0.03 | 1.6 | 1.6 | 13 | 0.25 |

[a,b,c,d,e]Means within a column with different superscript letters differ (P < .05)
[1]Total volatile fatty acids, mM
[2]Volatile fatty acids, moles/100 mol of C2 = acetate, C3 = propionate, Ci4 = isobutyrate, C4 = butyrate, Ci5 = isovalerate, C5 = valerate
[3]mL/24 h fermentation
[4]µMoles/24 h fermentation
[5]µMoles/24 h fermentation
[6]Contained 0.29% Sulfur on a DMB
[7]Contained 1.09% Sulfur on a DMB
[8]9, 10-Anthraquinone
[9]Rumensin (Ionophore)
[10]n = 3 administering to the ruminant at least one polycyclic quinone and at least one ionophore compound.

6. The method of claim 5 wherein the polycyclic quinone and the ionophore are administered to the ruminant approximately simultaneously.

7. The method of claim 5 wherein the polycyclic quinone further comprises an anthraquinone or anthrahydroquinone compound.

8. The method of claim 5 wherein the ionophore compound is selected from the group consisting of monensin sodium, lasalocid A, salinomycin, avoparcin, aridcin, actaplanin and penicillin.

9. The method of claim 5 wherein the quantity of the polycyclic quinone is approximately within the range of 10–500 ppm in rumen fluid of the ruminant.

10. The method of claim 5 wherein the quantity of the ionophore compound is approximately within the range of 0.5–35 ppm in rumen fluid of the ruminant.

11. A method for synergistically reducing methane formation in the rumen of a ruminant, the method comprising administering to the ruminant a composition comprising at least one polycyclic quinone and at least one ionophore compound.

12. The method of claim 11 wherein the polycyclic quinone further comprises an anthraquinone or anthrahydroquinone compound.

13. The method of claim 11 wherein the ionophore compound is selected from the group consisting of monensin sodium, lasalocid A, salinomycin, avoparcin, aridcin, actaplanin and penicillin.

14. The method of claim 11 wherein the quantity of the polycyclic quinone is approximately within the range of 10–500 ppm in rumen fluid of the ruminant.

15. The method of claim 11 wherein the quantity of the ionophore compound is approximately within the range of 0.5–35 ppm in rumen fluid of the ruminant.

* * * * *